United States Patent
Lyden et al.

(10) Patent No.: US 8,750,997 B2
(45) Date of Patent: Jun. 10, 2014

(54) IMPLANTABLE MEDICAL DEVICE INCLUDING ISOLATION TEST CIRCUIT

(75) Inventors: Michael J. Lyden, Shoreview, MN (US); Joseph M. Bocek, Seattle, WA (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 280 days.

(21) Appl. No.: 12/977,158

(22) Filed: Dec. 23, 2010

(65) Prior Publication Data

US 2011/0160808 A1 Jun. 30, 2011

Related U.S. Application Data

(60) Provisional application No. 61/291,718, filed on Dec. 31, 2009.

(51) Int. Cl.
*A61N 1/00* (2006.01)

(52) U.S. Cl.
USPC .......................................................... 607/27

(58) Field of Classification Search
USPC .......................................... 600/28, 116, 372
See application file for complete search history.

(56) References Cited

U.S. PATENT DOCUMENTS

| | | |
|---|---|---|
| 4,142,533 A | 3/1979 | Brownlee et al. |
| 4,332,256 A | 6/1982 | Brownlee et al. |
| 4,595,009 A | 6/1986 | Leinders |
| 4,785,812 A | 11/1988 | Pihl et al. |
| 4,800,883 A | 1/1989 | Winstrom |
| 4,821,723 A | 4/1989 | Baker, Jr. et al. |
| 5,002,052 A | 3/1991 | Haluska |
| 5,003,975 A | 4/1991 | Hafelfinger et al. |
| 5,224,475 A | 7/1993 | Berg et al. |
| 5,431,684 A | 7/1995 | Archer et al. |
| 5,453,698 A | 9/1995 | Williams et al. |
| 5,549,646 A | 8/1996 | Katz et al. |
| 5,571,156 A | 11/1996 | Schmukler |
| 5,591,218 A | 1/1997 | Jacobson |
| 5,626,619 A | 5/1997 | Jacobson et al. |
| 5,645,572 A | 7/1997 | Kroll et al. |
| 5,755,742 A | 5/1998 | Schuelke et al. |
| 5,891,179 A | 4/1999 | Er et al. |
| 5,897,577 A | 4/1999 | Cinbis et al. |
| 6,208,898 B1 | 3/2001 | Gliner et al. |
| 6,493,586 B1 | 12/2002 | Stahmann et al. |
| 6,668,193 B2 | 12/2003 | Ware et al. |

(Continued)

OTHER PUBLICATIONS

Berdyshev, S, et al., "Intracardiac Impedance as a Method for Ventricular Volume Monitoring—Investigation by a Finite-Element Model and Clinical Data", 2010 J. Phys.: Conf. Ser. 224 012095, (http://iopscience.iop.org/1742-6596/224/1/012095).

(Continued)

*Primary Examiner* — Christopher D Koharski
*Assistant Examiner* — Nadia Ahmad
(74) *Attorney, Agent, or Firm* — Schwegman, Lundberg, Woessner, P.A.

(57) ABSTRACT

An implantable medical device can include a hermetically-sealed implantable housing, an exposed first conductor located on or near the housing, and at least one insulated second conductor located near the exposed first conductor. In an example, the implantable medical device can include an isolation test circuit to provide a test stimulus to the exposed first conductor and configured to measure a portion of the test stimulus coupled to the second conductor.

20 Claims, 6 Drawing Sheets

(56) References Cited

U.S. PATENT DOCUMENTS

| | | | |
|---|---|---|---|
| 6,721,600 B2* | 4/2004 | Jorgenson et al. | ............... 607/27 |
| 7,047,083 B2 | 5/2006 | Gunderson et al. | |
| 7,050,851 B2 | 5/2006 | Plombon et al. | |
| 7,211,884 B1 | 5/2007 | Davis et al. | |
| 7,242,981 B2 | 7/2007 | Ginggen | |
| 7,283,863 B2 | 10/2007 | Gunderson et al. | |
| 7,289,851 B2 | 10/2007 | Gunderson et al. | |
| 7,369,898 B1 | 5/2008 | Kroll et al. | |
| 7,454,249 B1 | 11/2008 | Bornzin et al. | |
| 7,509,167 B2 | 3/2009 | Stessman | |
| 7,515,961 B2 | 4/2009 | Germanson et al. | |
| 7,522,957 B2 | 4/2009 | Ostroff | |
| 7,561,915 B1 | 7/2009 | Cooke et al. | |
| 7,574,259 B1 | 8/2009 | Pei et al. | |
| 7,623,930 B2 | 11/2009 | Zeijlemaker et al. | |
| 2002/0072769 A1 | 6/2002 | Silvian et al. | |
| 2002/0120307 A1 | 8/2002 | Jorgenson et al. | |
| 2002/0161406 A1 | 10/2002 | Silvian | |
| 2003/0088279 A1 | 5/2003 | Rissmann et al. | |
| 2003/0088282 A1 | 5/2003 | Ostroff | |
| 2004/0024424 A1 | 2/2004 | Propp et al. | |
| 2005/0288714 A1 | 12/2005 | Ostroff | |
| 2006/0167496 A1 | 7/2006 | Nelson et al. | |
| 2006/0293591 A1* | 12/2006 | Wahlstrand et al. | .......... 600/423 |
| 2007/0293903 A1 | 12/2007 | Bohn et al. | |
| 2008/0114410 A1 | 5/2008 | Ding et al. | |
| 2008/0147132 A1 | 6/2008 | Elahi et al. | |
| 2009/0138058 A1 | 5/2009 | Cooke et al. | |
| 2009/0157132 A1 | 6/2009 | Linder et al. | |
| 2009/0157137 A1 | 6/2009 | Gilkerson et al. | |
| 2009/0157146 A1 | 6/2009 | Linder et al. | |
| 2009/0177110 A1 | 7/2009 | Lyden et al. | |
| 2009/0210021 A1 | 8/2009 | Ostroff | |
| 2009/0319014 A1* | 12/2009 | Muecke et al. | ............... 607/126 |
| 2010/0030286 A1 | 2/2010 | Goetz et al. | |
| 2012/0158089 A1 | 6/2012 | Bocek et al. | |

OTHER PUBLICATIONS

Bernstein, Neil E, et al., "Right-sided implantation and subpectoral position are predisposing factors for fidelis lead fractures", Heart Rhythm, 6(5), Supplement, Abstract PO02-145, (May 2009), S192.

Calame, Susan, et al., "A Large Single Center Experience with Fidelis Lead Failure: Lower Impedance at Time of Lead Implantation Independently Associates with Lead Failure", Heart Rhythm, 6(5) Supplement, Abstract PO05-158, (May 2009), S385.

Ellenbogen, Kenneth A, et al., "Lead Integrity Alert Performance for Non-Sprint Fidelis® ICD Lead Fractures", Heart Rhythm, 6(5) Supplement, Abstract PO03-125, (May, 2009), S248-S249.

Jain, Sandeep K, et al., "Intensified Remote Monitoring in Medtronic Fidelis Patients", Heart Rhythm, 6(5) Supplement, Abstract PO05-156, (May 2009), S384.

Krahn, Andrew D, et al., "Acceleration of Fidelis Failure Rate in the Canadian Heart Rhythm Society Device Advisories Committee Registry", Heart Rhythm, 6(5) Supplement, Abstract AB35-1, (May 2009), S74-S75.

Kreuz, Jens, et al., "Detailed Electrical Analysis of Lead Failures in a Small Scaled Right Ventricular Defibrillator Lead: Reality of Sprint Fidelis Medical Device Recalls in a Single Centre", Heart Rhythm, 6(5), Supplement, Abstract PO02-126, (May 2009), S185.

Lyne, Jonathan C, et al., "High failure rate of sprint fidelis defibrillator lead in young/ACHD patients: the Brompton & Harefield experience", Heart Rhythm, 6(5), Supplement, Abstract AB12-1, (May 2009), S23.

Morrison, Thomas B, et al., "Risk Factors for Fidelis and non-Fidelis Implantable Defibrillator Lead Failure", Heart Rhythm, 6(5) Supplement, Abstract AB39-4, (May 2009), S84-S85.

Nguyen, Bich Lien, "High Sensing Integrity Counter with a Sprint FidelisTM Defibrillation Lead and a Cardiac Contractility Modulation Device: False Indication of High Voltage Lead Failure", Heart Rhythm, 6(5) Supplement, Abstract PO02-166, (May 2009), S200.

Patel, Amisha S, et al., "Modification to Lead Integrity Alert Improves Performance", Heart Rhythm, 6(5) Supplement, Abstract PO06-131, (May 2009), S438.

U.S. Appl. No. 13/297,785, filed Nov. 16, 2011, Lead Fault Detection for Implantable Medical Device.

"U.S. Appl. No. 13/297,785, Non Final Office Action mailed Jun. 26, 2013", 9 pgs.

"U.S. Appl. No. 13/297,785, Non Final Office Action mailed Dec. 26, 2013", 11 pgs.

"U.S. Appl. No. 13/297,785, Response filed Nov. 26, 2013 to Non Final Office Action mailed Jun. 26, 2013", 10 pgs.

* cited by examiner

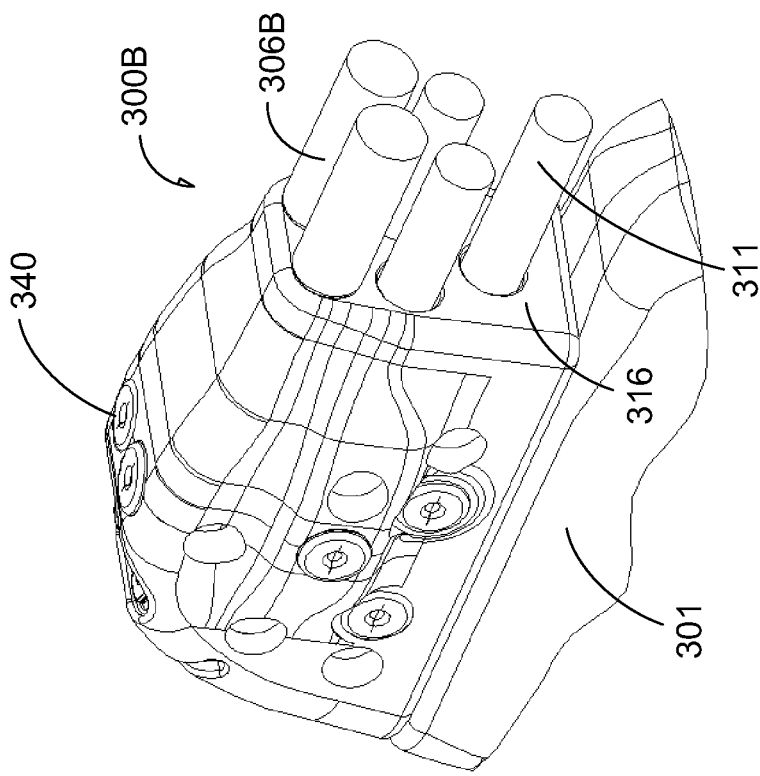
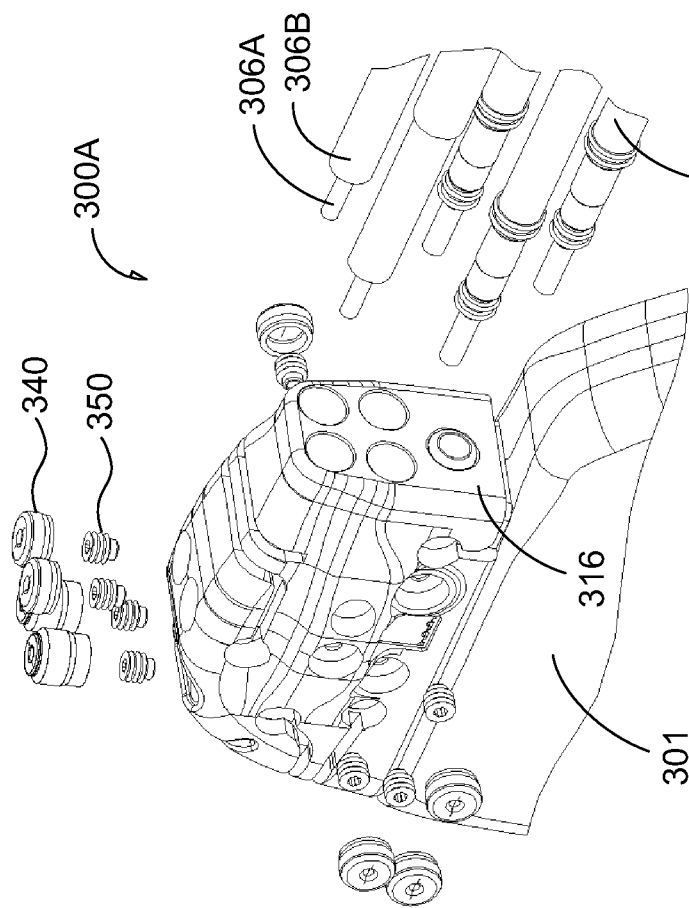

IMPLANTABLE MEDICAL DEVICE INCLUDING ISOLATION TEST CIRCUIT

CLAIM OF PRIORITY

This patent application claims the benefit of priority, under 35 U.S.C. Section 119(e), to Lyden, et al., U.S. Provisional Patent Application Ser. No. 61/291,718, entitled "Implantable Medical Device including Isolation Test Circuit," filed on Dec. 31, 2009, which is hereby incorporated by reference herein in its entirety.

BACKGROUND

Implantable medical devices (IMDs) can perform a variety of diagnostic or therapeutic functions. In an example, an IMD can include one or more cardiac function management features, such as to monitor the heart or to provide electrical stimulation to a heart or to the nervous system, such as to diagnose or treat a subject, such as one or more electrical or mechanical abnormalities of the heart. Examples of IMDs can include pacers, automatic implantable cardioverter-defibrillators (ICDs), cardiac resynchronization therapy (CRT) devices, implantable monitors, neuromodulation devices (e.g., deep brain stimulators, or other neural stimulators), cochlear implants, or drug pumps, among others.

Nuclear magnetic resonance imaging (MRI) is a medical imaging technique that can be used to visualize internal structure of the body. MRI is an increasingly common diagnostic tool, but can pose risks to a person with an IMD, such as a patient undergoing an MRI scan or a person nearby MRI equipment, or to people having a conductive implant.

In an MR field, an item, such as an IMD, can be referred to as "MR Safe" if the item poses no known hazard in all MRI environments. In an example, MR Safe items can include non-conducting, non-metallic, non-magnetic materials, such as glass, porcelain, a non-conductive polymer, etc. An item can be referred to as "MR Conditional" in the MR field if the item has been demonstrated to pose no known hazards in a specified MRI environment with specified conditions of use (e.g., static magnetic field strength, spatial gradient, time-varying magnetic fields, RF fields, etc.). In certain examples, MR Conditional items can be labeled with testing results sufficient to characterize item behavior in a specified MRI environment. Testing can include, among other things, magnetically induced displacement or torque, heating, induced current or voltage, or one or more other factors. An item known to pose hazards in all MRI environments, such as a ferromagnetic scissors, can be referred to as "MR Unsafe."

OVERVIEW

The present inventors have recognized, among other things, that IMDs can include or be coupled to long conductors, such as a leadwire carrying one or more distal electrostimulation or sensing electrodes contacting a desired tissue region of the patient. This can potentially be susceptible to developing a significant MRI gradient induced electromagnetic field (EMF), such as along electrodes located at a distal end of the leadwires and at the IMD case housing its electronics. MRI gradient induced EMF can also exist between significantly separated electrodes. Leadwires and other such elongated conductors included in or coupled to an IMD can also act as antenna, and can therefore also be susceptible to RF emissions from the MRI machine.

Some illustrative examples of IMDs that can include or be coupled to elongated electrical connections to the patient can include, but are not limited to, the following: (1) neuromodulators, such as deep brain stimulators (DBS), various pain control devices, or systems that can stimulate the spinal cord, muscle tissue, or other nerves of the body, e.g., a vagal nerve stimulator (VNS); (2) cardiac pacers; (3) automatic implantable cardioverter defibrillators (AICDs); (3) implantable diagnostic devices such as to monitor cardiac function, e.g., a loop recorder/Holter-monitor-like recording device; or (4) cochlear implants. The present subject matter, such as described in detail herein, can be applied to these and other ambulatory medical devices or IMDs.

Ambulatory or IMDs, such as a cardiac function management device, can include an "MRI mode," such as activated manually or automatically. The MRI mode can configure the device into an "MR Conditional" mode, such as including a non-sensing, fixed-rate pacing mode such as to maintain pacing therapy during an MRI scan. In an example, high-voltage tachyarrhythmia therapy (e.g., defibrillation shock) can be disabled in the MRI mode, such as to prevent inappropriate shocks from being administered by the device, with the patient being closely monitored during the MRI procedure, or to prevent unwanted torques or forces being exerted on the IMD or one or more other conductive implants.

In an example, the MRI mode may mitigate some of the hazards to a subject in or near an MR fields, such as generated by nuclear magnetic resonance (NMR) equipment (e.g., an NMR spectrometer, an MRI scanner, etc.). However, if the MRI mode is not configured automatically, this mitigation can need the intervention of an external programmer and an electrophysiologist, cardiologist, or likewise skilled medical professional capable of temporarily re-programming the device into the MRI mode. Moreover, some devices do not include an MRI mode.

In an example, an IMD can be conditionally safe in an MRI environment, such as an IMD lacking a unipolar pacing lead configuration. For example, a conditionally MRI-safe IMD can include only bipolar pacing or sensing capabilities, or can use a bipolar pacing mode, such as rather than a unipolar pacing mode, such as during exposure to an MRI environment. However, the present inventors have recognized that one or more of a lead insulation defect, or an exposed conductor on the IMD, such as located on or within a header block attached to the IMD, or one or more other defects, can create a large loop area.

For example, the large loop area can make the IMD more vulnerable to unwanted disruption or coupling of one or more time-varying externally-applied magnetic fields even when the IMD is configured in a bipolar pacing mode, or with pacing or shock outputs disabled, for example. Thus, in an example, an IMD can include one or more diagnostic features, such as to test isolation between one or more conductors, such as between a conductive region near or including the housing of the IMD and one or more other conductors, such as one or more connections on or within the header block of the IMD. In an example, an alert or warning can be generated, such as to warn a patient or caregiver that the IMD is not in a conditionally MRI-safe mode. In an example, the isolation test can be triggered automatically, such as at specified times, or upon detection of a magnetic field having an intensity above a specified threshold, or manually, such as by the patient or caregiver.

The IMD can include a hermetically-sealed implantable housing, an exposed first conductor located on or near the housing, and at least one insulated second conductor located near the exposed first conductor. In an example, the implantable medical device can include an isolation test circuit to provide a test stimulus to the exposed first conductor and configured to measure a portion of the test stimulus coupled to the second conductor.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIGS. 3A-B illustrate generally examples of portions of an implantable medical device, including a header block, shown in an exploded and assembled view.

DETAILED DESCRIPTION

Figure 1:
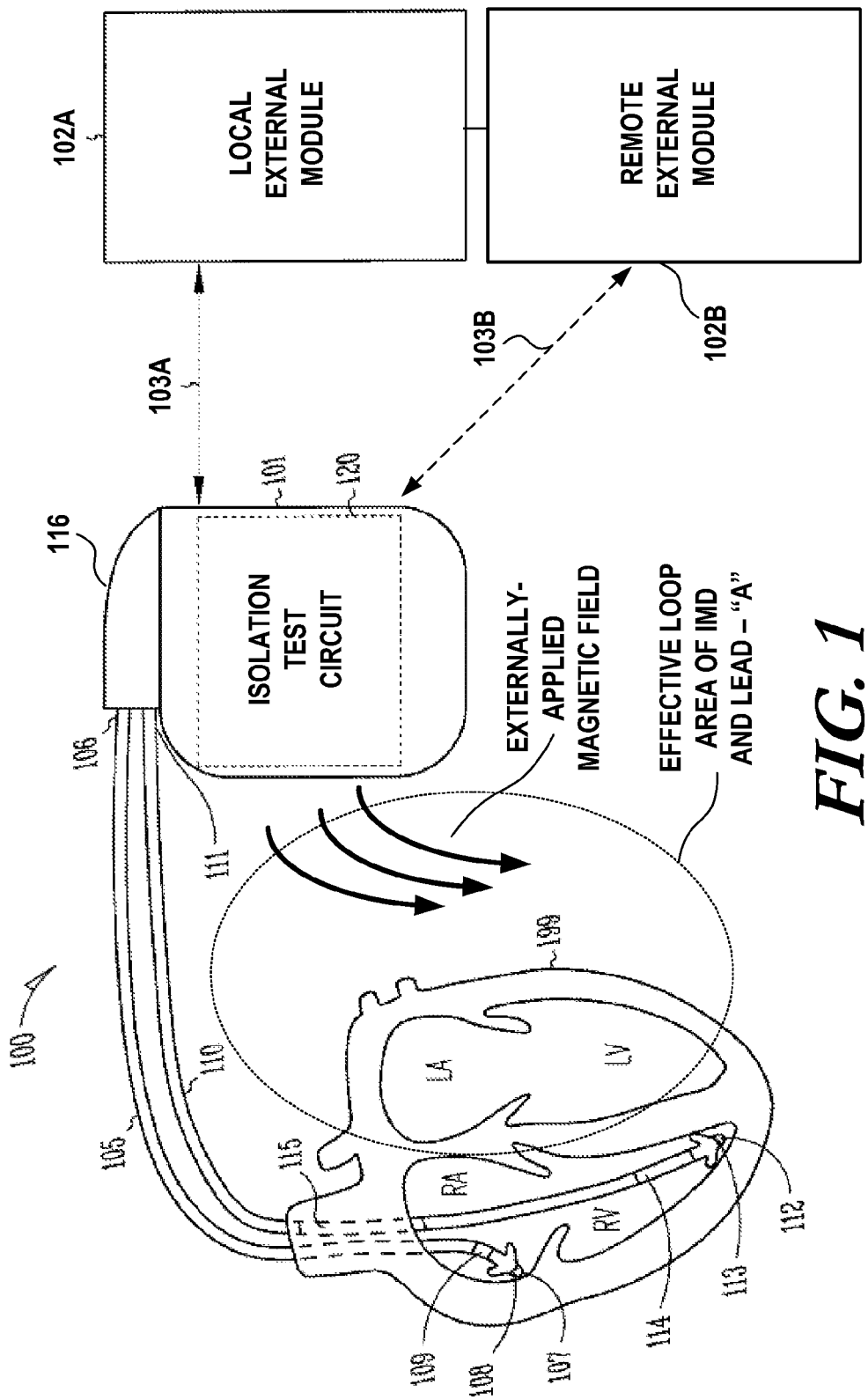
FIG. 1 illustrates generally an example of at least a portion of a cardiac functional management system including an implantable medical device.

Nuclear magnetic resonance (NMR) devices (e.g., an MRI scanner, an NMR spectrometer, or other NMR device) can produce both static and time-varying magnetic fields. For example, an MRI scanner can provide a strong static magnetic field, $B_0$, such as to align nuclei within a subject to the axis of the $B_0$ field. The $B_0$ can provide a slight net magnetization (e.g., a "spin polarization") among the nuclei in bulk because the spin states of the nuclei are not randomly distributed among the possible spin states. Because the resolution attainable by NMR devices can be related to the magnitude of the $B_0$ field, a stronger $B_0$ field can be used to spin polarize the subject's nuclei to obtain finer resolution images. NMR devices can be classified according the magnitude of the $B_0$ field used during imaging, such as a 1.5 Tesla $B_0$ field, a 3.0 Tesla $B_0$ field, etc.

After nuclei are aligned using the $B_0$ field, one or more radio frequency (RF) magnetic excitation pulses can be delivered such as to alter the alignment of specified nuclei (e.g., within a particular volume or plane to be imaged within the subject). The power, phase, and range of frequencies of the one or more RF excitation pulses can be selected, such as depending on the magnitude of the $B_0$ field, the type or resonant frequency of the nuclei to be imaged, or one or more other factors. After the RF excitation pulses are turned off, one or more RF receivers can be used to detect a time-varying magnetic field (e.g., a flux) developed by the nuclei as they relax back to a lower energy state, such as the spin polarized state induced by the static magnetic field, $B_0$.

One or more gradient magnetic fields can also be provided during MR, such as to create a slight position-dependent variation in the static polarization field. The variation in the static polarization field slightly alters the resonant frequency of the relaxing nuclei, such as during relaxation after excitation by the one or more RF pulses. Using the gradient field along with the static field can provide "spatial localization" of signals detected by the RF receiver, such as by using frequency discrimination. Using a gradient field allows a volume or plane to be imaged more efficiently. In a gradient field example, signals received from relaxing nuclei can include energy in respective unique frequency ranges corresponding to the respective locations of the nuclei.

Active MRI equipment can induce unwanted torques, forces, or heating in an IMD or other conductive implant, or can interfere with operation of the IMD. In certain examples, the interference can include disruption in sensing by the IMD, interference in communication between the IMD and other implants or external modules during MRI operation, or disruption in monitoring or therapeutic function of the IMD.

During an MRI scan, the one or more RF excitation pulses can include energy delivered at frequencies from less than 10 MHz to more than 100 MHz, such as corresponding to the nuclear magnetic resonances of the subject nuclei to be imaged. The gradient magnetic field can include energy delivered at frequencies lower than the RF excitation pulses, because most of the AC energy included in the gradient field is provided when the gradient field is ramping or "slewing." The one or more gradient magnetic fields can be provided in multiple axes, such as including individual time-varying gradient fields provided in each of the axes to provide imaging in multiple dimensions.

In an example, the static field, $B_0$, can induce unwanted forces or torques on ferromagnetic materials, such as steel or nickel. The forces or torques can occur even when the materials are not directly within the "bore" of the MRI equipment—because significant fields can exist near the MRI equipment. Moreover, if an electric current is switched on or off in the presence of the $B_0$ field, a significant torque or force can be suddenly imposed in the plane of the circulation of the current, even though the $B_0$ field itself is static. The induced force or torque can be minimal for small currents, but the torque can be significant for larger currents, such as those delivered during defibrillation shock therapy. For example, assuming the circulating current is circulating in a plane normal (e.g., perpendicular) to the static field, the torque can be proportional to the magnitude of the $B_0$ field, multiplied by the surface area of the current loop, multiplied by the current.

Time-varying fields, such as the gradient field or the field associated with the RF excitation pulse, can present different risks than the static field, $B_0$. For example, the behavior of a wire loop in the presence of a time-varying magnetic field can be described using Faraday's law, which can be represented by $$\varepsilon = -\frac{d\Phi_{B_1}}{dt},$$

in which ε can represent the electromotive force (e.g., in volts), such as developed by a time-varying magnetic flux. The magnetic flux can be represented as $$\Phi_{B1} = \int\int_S B_1 \cdot dS,$$

in which $B_1$ can represent an instantaneous magnetic flux density vector (e.g., in Webers per square meter, or Tesla). If $B_1$ is relatively uniform over the surface S, then the magnetic flux can be approximately $\Phi_{B1}=|B_1||A|$, where A can represent the area of the surface S. Operating MRI equipment can produce a time-varying gradient field having a slew rates in excess of 100 Tesla per second (T/s). The slew rate can be similar to a "slope" of the gradient field, and is thus similar to $$\frac{d\Phi_{B_1}}{dt}.$$

The electromotive force (EMF) of Faraday's law can cause an unwanted heating effect in a conductor—regardless of whether the conductor is ferromagnetic. EMF can induce current flow in a conductor (e.g., a housing of the IMD, one or more other conductive regions within the IMD, or one or more other conductive implants). The induced current can dissipate energy and can oppose the direction of the change of the externally applied field (e.g., given by Lenz's law). The induced current tends to curl away from its initial direction, forming an "eddy current" over the surface of the conductor, such as due to Lorentz forces acting upon electrons moving through the conductor. Because non-ideal conductors have a finite resistivity, the flow of induced current through the conductor can dissipate heat. The induced heat can cause a significant temperature rise in or near the conductor over the duration of the scan. The power dissipated by the eddy current can be proportional to the square of both the peak flux density and the frequency of the excitation.

Generally, induced currents, such as induced by the RF magnetic excitation pulse, can concentrate near the surface of a conductor, a phenomenon that can be referred to as the skin effect. The skin effect can limit both the magnitude and depth of the induced current, thus reducing power dissipation. However, the gradient field can include energy at a much lower frequency than the RF magnetic excitation field, which can more easily penetrate through the housing of the IMD. Unlike the field from the RF excitation pulse, the gradient field can more easily induce bulk eddy currents in one or more conductors within the IMD housing, such as within one or more circuits, capacitors, batteries, or other conductors.

Aside from heating, the EMF can create, among other things, non-physiologic voltages that can cause erroneous sensing of cardiac electrical activity, or the EMF can create a voltage sufficient to depolarize cardiac tissue or render the cardiac tissue refractory, possibly affecting pacing therapy. In an illustrative example, the IMD can be connected to one or more leads, such as one or more subcutaneous or intravascular leads positioned to monitor the patient, or to provide one or more therapies to the patient. In this illustrative example, a surface area of a "circuit" including the lead, the housing of the IMD, and a path through at least partially conductive body tissue between an electrode on the lead and the IMD housing can be more than 300 square centimeters, or more than 0.03 square meters. Thus, using Faraday's law, the electromotive force (EMF) developed through the body tissue between the electrode (e.g., a distal tip or ring electrode) of the lead and the housing of the IMD can be more than 0.03 square meters times 100 t/s, or more than 3 volts.

FIG. 1 illustrates generally an example of at least a portion of a cardiac functional management system 100, such as including an implantable medical device (IMD) 101. The IMD can include one or more of a pacemaker, an automatic implantable cardioverter defibrillator (ICD), a cardiac resynchronization therapy device, or other implantable cardiac function management device. While the example of FIG. 1 shows an IMD, such as a cardiac function management device, the discussion can also be relevant to other types of IMDS, such as attached to elongated leads or conductors, such as in other locations (e.g., in an example of a neurostimulator such as attached to one or more elongated electrostimulation leads located in or near the spine, brain, or elsewhere).

In an example, the IMD 101 can be electrically coupled to a heart 199 such as using one or more leads, such as a first lead 105 or a second lead 110. One or more external modules can communicate with the IMD 101, such as a local external module 102A (e.g., a bedside monitor, a patient-worn monitor, a physician programmer, or the like), or a remote external module 102B (e.g., a remote server or web-based user interface such as included on a personal computer, etc.). One or more external modules can transfer information, such as physiologic information, device configuration information, or other data between the IMD 101 and the respective local or remote external modules 102A and 102B, such as using a first or second respective communication link 103A or 103B. In an example, the respective communication links 103A or 103B can be wireless (e.g., acoustic, electromagnetic, magnetic, optical, etc.) or wired (e.g., using body conduction, or one or more other wired networking links).

In an example, the IMD 101 can include a hermetically sealed housing, such as containing, at least in part, electronic circuitry. In an example, the circuitry can include one or more portions, such as a circuit to sense or condition physiological signals, or a circuit to provide one or more electrostimulation therapies (e.g., to one or more cardiac or neural targets). In an example, the hermetically sealed housing itself can also function as an electrode for use in sensing physiologic information (e.g., electrically or mechanically), or for use as an electrode for electrostimulation delivery.

In an example, the first lead 105 can be used as a pacing lead, such as including a proximal end 106 connected to IMD 101 and a distal end 107, such as placed in the right atrium (RA) of heart 199. An atrial tip electrode 108 can be located at the distal end 107. In the example of FIG. 1, an atrial ring electrode 109 can located near distal end 107 as well. In an example, the respective tip and ring electrodes 108 and 109 can be electrically connected to IMD 101, such as via separate conductors in lead 105, such as to provide bipolar sensing of the atrial cardiac activity or bipolar delivery of atrial pacing pulses. In an example, the one or more separate conductors in lead 105 can be attached or secured to one or more terminal blocks included in a header block 116, such as to provide electrical contact between the lead 105 conductors, and circuitry within the IMD 110. In an example, the IMD 110 can be attached to one or more other leads or conductors, such as when the IMD 110 includes a cardiac resynchronization therapy (CRT) circuit. In a CRT example, the IMD 110 can be attached to one or more leads configured for intravascular delivery to a great vein of the heart, such as through the ostium of the coronary sinus, such as to provide pacing or sensing at various locations near the left ventricle of the heart.

In an example, the atrial tip electrode 108 can be used along with the housing of the IMD 101, such as to provide unipolar sensing of atrial cardiac activity, or unipolar delivery of atrial pacing pulses. In an example, the IMD 110 can include one or more circuits or programmable parameters allowing the IMD to be controllably configured for unipolar or bipolar pacing or sensing.

In an example, the second lead 110 can be a endocardial defibrillation lead, such as including a proximal end 111 connected to IMD 101 and a distal end 112, such as placed in the right ventricle (RV) of heart 199. For example, the second lead 110 can include a right ventricular (RV) distal tip electrode, such as located at or near the apical region of the RV chamber, near the distal end 112 of the RV lead.

In FIG. 1, An RV coil electrode 114 can be located near distal end 112 but can be electrically separated from the RV distal tip electrode 113. In an example, a superior vena cava (SVC) coil electrode 115 can be located at a distance from distal end 112.

In an example, the respective electrodes 113-115 can be electrically connected to IMD 101, such as via separate conductors in lead 110, such as attached or secured to one or more terminal blocks included in the header block 116 of the IMD. For example, the respective RV tip electrode 113 and RV coil electrode 114 can be used for bipolar sensing of the ventricular cardiac electrical activity or for delivery of ventricular electrostimulation pulses. In an example, one or more of the RV coil electrode 114, the SVC coil electrode 115, or the device housing can be used for sensing of cardiac electrical activity or for delivery of ventricular tachyarrhythmia therapy (e.g., one or more of anti-tachyarrhythmia pacing, cardioversion, shock, or the like).

One or more of the first or second communication links 103A or 103B can provides wireless information transmission between the IMD 101 and various implanted or external devices. For example, one or more of real-time physiological data acquired by IMD 101, physiological data acquired by and stored in IMD 101, therapy history data stored in IMD 101, information indicating an operational status of IMD 101 (e.g., battery status and lead impedance), or other information can be transferred. In an example, information transferred to the IMD 101 can include instructions programming IMD 101 to acquire physiological data, programming IMD 101 to perform at least one self-diagnostic test (such as for a device operational status, or an isolation test), programming IMD 101 to run a signal analysis algorithm (e.g., an algorithm implementing a tachyarrhythmia classification method) or programming IMD 101 to deliver one or more pacing or tachyarrhythmia therapies, among other instructions.

In an example, the internal circuitry of IMD 101, including its various elements discussed in this document, can include a combination of hardware and software. For example, one or more portions, elements, or circuits included in IMD 101 can be implemented, such as using an application-specific circuit constructed to perform one or more particular functions or a general-purpose circuit programmed to perform such function(s). Such a general-purpose circuit can include, but is not limited to, a microprocessor or a portion thereof, a microcontroller or portions thereof, and a programmable logic circuit or a portion thereof. For example, a "comparator" includes, among other things, an electronic circuit comparator constructed to perform the only function of a comparison between two signals or a portion of a general-purpose circuit driven by a code instructing that portion of the general-purpose circuit to perform the comparison between the two signals.

In an example, the IMD 101 can be in or near operating nuclear magnetic resonance devices. In a unipolar mode, such as using the housing of the IMD 110 as an electrode for pacing, sensing, or tachyarrhythmia therapy, a large effective loop area, "A," can exist. Similarly, when one or more defects expose one or more conductors near the housing of the IMD 110 to bodily fluid or tissue, the large loop area, "A," can also exist. It is believed that the loop area A might make the IMD 101 more vulnerable to external sources of interference, such as an externally applied magnetic field (e.g., one or more fields used during MRI scanning or by an NMR device), such as compared to a device using bipolar pacing or sensing, or having bipolar pacing or sensing disabled. Such interference can create erroneous sensed events, tissue or conductor heating, or might even be able to induce currents sufficient to provide unwanted electrostimulation at one or more electrodes attached to the IMD 101.

One approach can include programming the IMD 101 to a non-ambulatory mode, such as for temporary use during MRI scanning or when the IMD is operated near an NMR device. For example, the IMD can be programmed to bipolar-only pacing mode, such as used by one or more of the first lead 105 or the second lead 110. In the bipolar-only mode, the effective loop area of the electrostimulation and current return path (e.g., formed by one or more respective pairs of tip and ring electrodes) can be less than the loop area in a corresponding unipolar mode. However, a lead insulation failure, a seal plug or a core defect in the header, or one or more other defects, can expose one or more conductors near the housing of the IMD 101 to body tissue, effectively growing the loop area of the stimulation or sensing circuit, such as including one or more leads and the IMD 101.

The present inventors have recognized, among other things, that an undetected exposed conductor near the housing of the IMD 101 can cause the IMD 101 to behave as if it were in a unipolar mode, even though the IMD 101 can be programmed in a bipolar mode, possibly making the IMD 101 more vulnerable to interference, unwanted heating, or unwanted electrostimulation as discussed above.

In an example, the IMD 101 can be programmed to perform one or more diagnostic tests prior to exposure to MRI fields, either automatically, or manually, such as upon a command from the caregiver or patient. In an example, the IMD can include an isolation test circuit 120, such as configured to test for electrical leakage, lead insulation breach or failure, a lack of hermeticity or reduced hermiticity, or ingress of bodily fluids into an interior aperture or cavity within one or more of the first lead 105, the second lead, 110, or one or more parts, portions, or components of the IMD 101, such as the header block 116, or the housing of the IMD 101.

In an example, the IMD 101 can provide an alert or warning to the patient or caregiver, such as when unacceptable electrical leakage is detected. Such a warning or alert can be provided acoustically (e.g., a beeper or buzzer emitting a sound directly from IMD 101), mechanically (e.g., through muscle stimulation, such as using one or more electrodes located near the IMD 101 housing or header block 116), or using one or more of the first or second communication links 103A or 103B, such as to provide an audible or visual alert on one or more of the local external module 102A or the remote external module 102B.

Figure 2:
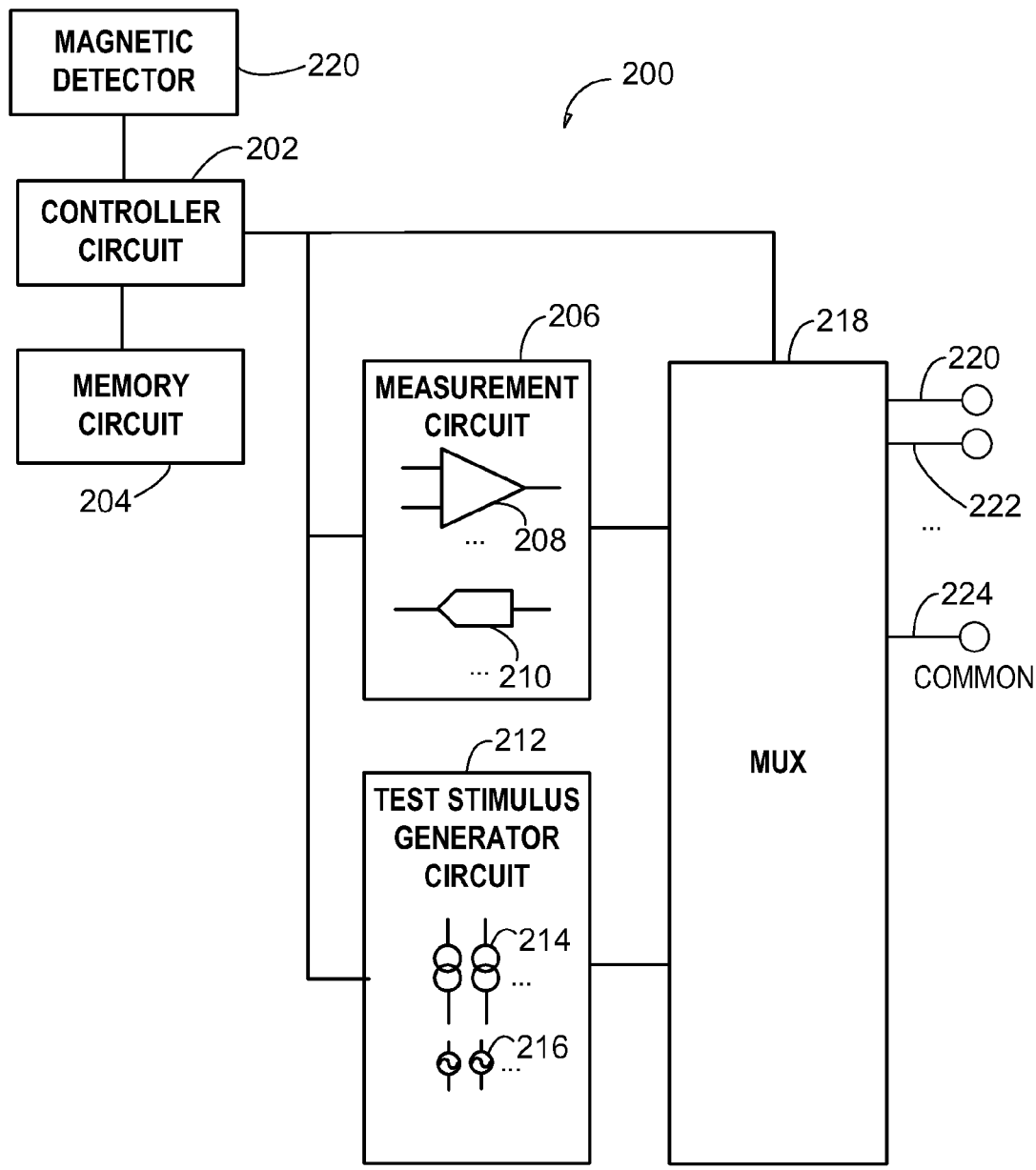
FIG. 2 illustrates generally an example of at least a portion of an implantable medical device, such as a cardiac function management device, such as including an isolation test circuit.

FIG. 2 illustrates generally an example of at least a portion of an implantable medical device, such as a cardiac function management device, such as including an isolation test circuit 200. In FIG. 2, the isolation test circuit can include one or more of a controller circuit 202, a memory circuit 204, a measurement circuit 206, a test stimulus generator circuit 212, or a multiplexer 218, such as coupled to one or more conductors, such as a first conductor 220, a second conductor 222, or a common conductor 224. In an example, the common conductor can be commonly shared with one or more other circuits, such as included in the IMD, such as an electrode included in or near a header block of the IMD, such as discussed in FIGS. 1, 3A-B, and 4-5.

In an example, such as shown in FIG. 2, the measurement circuit can include one or more filters, amplifiers, comparators, or analog-to-digital converters (ADCs), such as a comparator 208, or an ADC 210, such as to monitor or receive one or more voltages or currents. For example, the controller circuit 202 can be used to configured an operating mode of the measurement circuit 206, such as to digitize or capture one or more of a voltage, a current, an impedance, or one or more other parameters derived from the voltage, current, or impedance, such as for temporary or long-term storage in the memory circuit 204.

In an example, such as shown in FIG. 2, the test stimulus generator circuit can include one or more sources such as a voltage source 216, or a current source 214, such as to provide an isolation test stimulus signal to one or more of the respective conductors 220, 222, or 224. In an example, one or more portions of the respective measurement or test stimulus generator circuits 206 or 212 can be commonly shared, such as with one or more respective cardiac electrical activity or impedance sensing circuits, or one or more respective electrostimulation circuits such as included in the IMD. In an example, a portion of the multiplexer 218 can be commonly shared with a pacing lead configuration switch matrix, or a with a defibrillation shock output circuit, such as included in the IMD.

In an example, one or more of the measurement circuit 206 or the test stimulus generator circuit 212 can include multiple channels, and the multiplexer 218 can be omitted, made simpler, or can be used to provide stimulus signals or measurements for multiple conductors, simultaneously or independently.

In an example, the controller circuit 202 can be configured to process information from the measurement circuit 206, such as to determine a mean, median, average (e.g., a moving average or a long-term average), or other central tendency of the information from the measurement circuit 206. In an example, the controller circuit 202 can be configured to process the information from the measurement circuit 206 such as to determine degree of dispersion or variation in information from the measurement circuit 206, such as a standard deviation, variance, or other statistic. In an example, the measurement circuit 206 can compare a measured parameter, such as a voltage, impedance, or a current, to a specified threshold value, and the controller circuit can generate an alert when the voltage, impedance, or current is outside a specified range, such as established by the specified threshold value.

The isolation test circuit 200 can be configured to run one or more isolation tests automatically, such as during ambulatory operation of the IMD, or upon a command from a user such as patient or caregiver. In an example, information from a magnetic detector 220 (e.g., an inductor or transformer core saturation detector, a Hall effect sensor, or one or more other sensors such as included in measurement circuit 206 or elsewhere), can be used to trigger an isolation test, or to increase one or more of a frequency or duration of successive isolation tests. In an example, such a test can be triggered when the magnetic field exceeds a specified threshold (e.g., an intense magnetic field, such as produced by MRI equipment, NMR equipment, electrical heavy machinery, or one or more other sources). An example of using a Hail effect sensor in an implantable medical device to sense a magnetic field is described in Linder et al. U.S. Patent Pub. No. 20090157146, now issued as U.S. Pat. No. 8,121,678, entitled IMPLANTABLE MEDICAL DEVICE WITH HALL SENSOR, assigned to Cardiac Pacemakers, Inc, which is incorporated herein by reference in its entirety, including its description of using a Hall-effect sensor to detect a magnetic field, such as that of an .MRI scanner. An example of using a Haft-effect sensor in conjunction with an MRI operating mode of an implantable medical device is described in Cooke et al. U.S. Patent Pub, No. 20090138058, now issued as U.S. Pat. No. 8,014,867, entitled MRI OPERATION MODES FOR IMPLANTABLE MEDICAL DEVICES, which is assigned to Cardiac Pacemakers, Inc., which is incorporated herein by reference in its entirety, including its description of using a Hall-effect sensor in conjunction with an MRI operating mode of an implantable medical device.

In an example, the magnetic detector 220 can additionally or alternatively include an inductor saturation detector, such as to detect the presence of an MR field indicative of an MR scanner performing an MR scanning operation nearby. An example of using inductor saturation to perform MRI detection is described in Stessman, U.S. Pat. No. 7,509,167, entitled MRI DETECTOR FOR AN IMPLANTABLE MEDICAL DEVICE, assigned to Cardiac Pacemakers, Inc., which is incorporated herein by reference in its entirety, including its description of using inductor saturation to perform MRI detection.

For example, a voltage or current can be sourced, such as using the common conductor 224 (e.g., located at or near a header or connector block of the IMD). In an example, the housing of the IMD or other node can be the reference node for the voltage to be sourced, or can be one of the electrodes at which stimulus current is either sourced or sunk. Then, in an example, one or more of a coupled voltage or sunk current can be detected at another conductor, such as the first or second conductors 220 or 222, such as measured with respect the housing of the IMD. Thus, in an example, the housing of the IMD can be used as both a stimulus electrode, and as a measurement electrode, such as described in the examples of FIG. 7. In an example, the first or second conductors 220 or 222 can be attached to respective first and second electrodes, such as included at a distal end of an implantable lead, such as shown in FIG. 1. The common electrode 224 can be more proximal to the IMD itself, such as in or near the header block of the IMD. In an example, the test stimulus generator circuit can provide a small AC voltage at the common electrode 224. When the IMD is programmed in a bipolar pacing mode, the small AC voltage should not be strongly detected at the distal first or second electrodes, such as attached to the first or second conductors 220 or 222. For example, the small AC voltage coupled to the distal electrodes can be measured by the measurement circuit 206, and compared to a threshold. If the coupled AC voltage is at or below a specified voltage threshold, then the integrity of the header and lead insulation can be verified, at least for low voltage operation. However, if the lead insulation is defective, or if a conductive region is exposed near the IMD housing or header block (e.g., closer to the common electrode 224), the coupled AC voltage can exceed the specified voltage threshold, such as indicating a defect in the lead insulation, or a missing seal plug, etc.

In an example, a voltage can be provided by the common electrode 224 by the test stimulus generator circuit 212, and the isolation test circuit can scan all other conductors, such as attached to the mux 218, to determine each conductor, if any, where the coupled voltage exceeds the specified voltage threshold. In an example, multiple voltage thresholds can be used, such as one or more higher thresholds for conductors coupled to electrodes more proximal to the IMD housing or header block, and correspondingly lower thresholds for more distal electrodes.

In an example, the test stimulus generator circuit 212 need not be used to provide stimulus. For example, the measurement circuit 206 can be used to measure a baseline DC or AC voltage, such as across one or more conductors including the first, second, or common conductors 220, 222, or 224. In an example, a lead insulation defect, a missing seal plug, or direct exposure of a conductor to bodily fluid can increase a baseline voltage detected across two respective conductors, such as caused by increased myopotentials coupled to the conductors.

In an example, both current injection and voltage measurement can be used simultaneously, such as generated by the stimulus circuit 221 or measured by the measurement circuit 206, such as to determine an impedance between one or more conductors. Similar to the examples above, an AC impedance measurement can be made, such as by injecting a current between the common electrode 224 and one or more other conductors, such as one or more of the first or second conductors 220 or 222, and measuring the voltage developed across the respective conductors. In an example, a synchronous current injection and voltage measurement can be used, such as discussed in relation to the physiologic impedance measurement techniques of U.S. Patent Pub. No. 20090177110 (U.S. patent application Ser. No. 12/350,728), entitled "IMPEDANCE MEASUREMENT AND DEMODULATION USING IMPLANTABLE DEVICE," filed on Jan. 8, 2009, assigned to Cardiac Pacemakers, Inc., which is herein incorporated by reference in its entirety, including its description of injecting one or more non-tissue-stimulating bi-phasic current pulses and synchronously measuring the voltage induced by the one or more bi-phasic current pulses.

In an example, a series of successive impedance measurements can be made, such as between one or more of the first or second conductors 220 or 222, such as connecting to the one or more distal electrodes, and the common electrode 224 (e.g., located in or near the header of the IMD, or such as the housing itself). For example, if the impedance between one or more of the first or second conductors 220 or 222 and to the common electrode 224 is fluctuating, or drops below a specified minimum impedance, an alert or warning can be generated. In an example, one or more portions or components of the measurement circuit 206 or the stimulus circuit 212 can be commonly shared with an ambulatory lead impedance measurement circuit, such as used to monitor one or more lead impedances corresponding to one or more leads attached to the IMD.

In an example, the controller circuit 202 can log an alert, such as storing one or more episodes or alerts in the memory circuit 204, such as when a measured impedance between two or more conductors is erratic or falls outside one or more relative indications (e.g., a ratio or percentage, or an indication of spread such as a standard deviation or a variance) or an absolute range. For example, if the measured impedance falls outside a specified range or is otherwise erratic (e.g., drops or increases 25% or more), such as during a series of impedance measurements made during the specified duration (e.g., during months, weeks, days, hours, or during an acute diagnostic session of seconds or minutes, etc.), an alert can be generated, such as allowing a caregiver to postpone or cancel any exposure of the IMD to NMR devices or MRI scanning fields, or other sources of interference (e.g., ablation, electrocautery, etc.). Similarly, in an example, an alert can be generated if a present impedance measurement deviates considerably from an immediately previous impedance measurement, or if the measured impedance falls outside a specified range such as defined by an indication of spread (e.g., a standard deviation range, a variance range). In an example, an alert can be generated if one or more impedance measurements are erratic or deviate from one another by more than a specified relative amount or absolute amount. Note that an impedance increase can also indicate an insulation breach or other fault, so the examples discussed above can be equally applied to an impedance increase, or to erratic increases or decreases in impedance or other measured electrical parameters (e.g., due to a lead fracture, an open circuit, etc.).

FIGS. 3A-B illustrate generally examples of portions of an implantable medical device (IMD) 301, such as including a header block 316, shown in an exploded (e.g., FIG. 3A) and an assembled view (e.g., FIG. 3B). The header block 316 of FIGS. 3A-B can be formed from a biocompatible material, such as a molded thermoplastic polyurethane (e.g., TECOTHANE™), or from one or more other materials, such as to provide one or more secure electrical or mechanical connections between one or more leads such as a first lead 311, and the IMD. In an example, a second lead can include a flexible insulating jacket 306B, such as including silicone or one or more other flexible or elastic biocompatible materials, such as insulate an interior conductor 306A, such as when the lead is exposed to bodily fluid or tissue. One or more of the first lead 311 or second lead 306A-B can be inserted into a corresponding cavity (e.g., a lead "bore") in the header block 316. A set screw 350 can then be inserted or tightened, such as to secure the lead to a terminal block, such as including one or more electrical connections to circuitry within the IMD 301 such as shown in FIGS. 4-5.

In an example, one or more seal plugs 340 can be included, either separate from the set screw 350, or overmolded or encapsulated around a portion of the set screw 350. For example, one or more seal plugs 340 can be formed, molded, or stamped, such as using silicone or another flexible and biocompatible material, such as to isolate one or more electrical or mechanical connections internal to the header block 316 from bodily fluid or tissue surrounding the header 316, such as when the IMD 301 is implanted. One or more other exposed apertures or cavities, such as included in the header block 316 can be filled with medical adhesive (MA), such as a biocompatible curing silicone-based adhesive. In an example, one or more of a seal plug, MA adhesive fill, or lead insulation 306B can include one or more defects, or can be missing, such as omitted during manufacturing, or dislodged before, during, or after implant. In these examples, one or more of the circuits or techniques discussed in FIGS. 1, 2, 4-6 can be used, such as to detect a loose or missing seal plug 340, a dislodged header block 316, or one or more lead or insulation defects, such as a defect in insulating jacket 306B in a region near the IMD 301 housing or header block 316. In an example, one or more of a housing of the IMD 301 or an exposed electrode included in the header block 316 (e.g., a common electrode 224 as shown in FIG. 2) can be used, such as by the isolation test circuit of FIG. 2, such as to detect the one or more defects.

Figure 4:
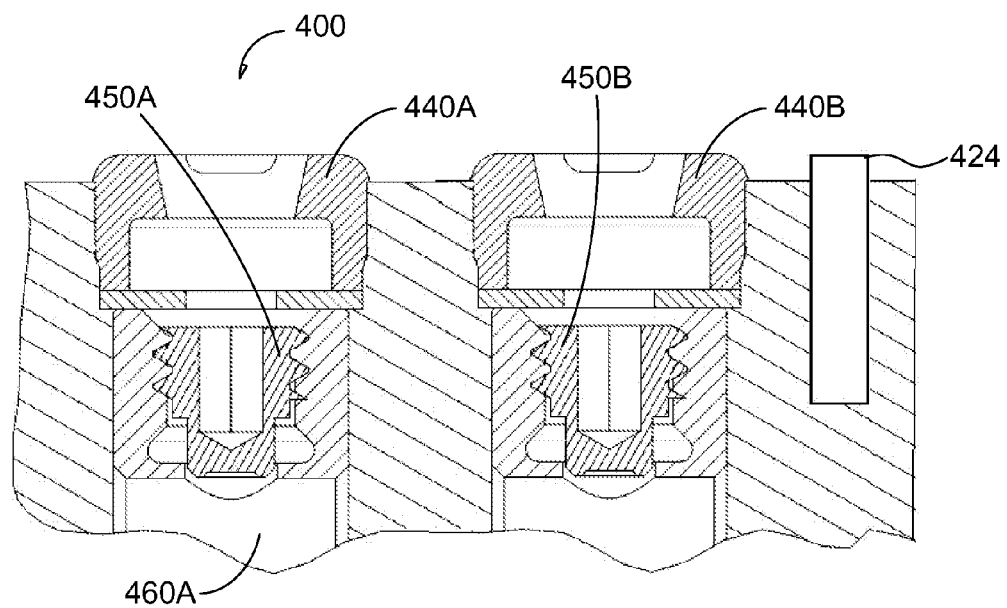
FIG. 4 illustrates generally an example of a section view of a portion of an implantable medical device, such as including a header block, a first seal plug and a first set screw, and a second seal plug and a second set screw.
Figure 5:
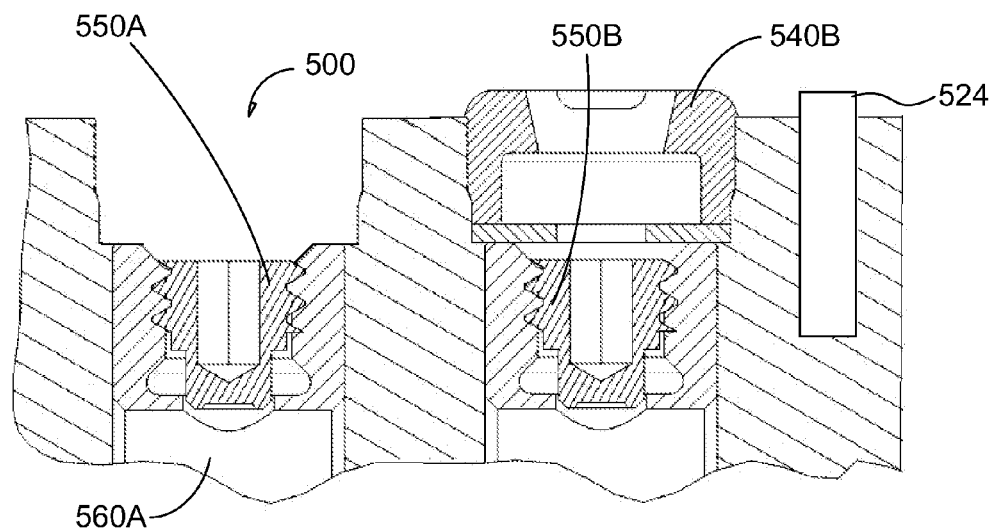
FIG. 5 illustrates generally an example of a section view of a portion of an implantable medical device, such as including a header block, a first set screw, and a seal plug, and a second set screw.

FIG. 4 illustrates generally an example of a section view of a portion of an implantable medical device, such as including a header block 400, a first seal plug 440A, a first set screw 450A, a second seal plug 440B, and a second set screw 450B. Similar to the example of FIG. 3, one or more set screws such as the first set screw 450A can secure or mechanically anchor an implantable lead in the header block 400, such as by displacing portion of a terminal block 460A. The first seal plug 440A can allow the set screw 450A to be torqued, such as via a self-closing slit in the seal plug 440A. However, one or more of the seal plugs 440A or 440B can leak, or fail to seal the respective first or second set screws 460A-B, such as exposing one or more of the set screws 460A-B to conductive bodily fluids or tissue.

In an example, one or more of the circuits or techniques discussed in FIG. 1, 2, 3A-B, or 5-6 can be used, such as to detect a loose or missing seal plug, such as the first or second seal plugs 440A-B, or one or more other defects, such as providing an unwanted conductive path, such as through body tissue or fluid, such as between set screws 450A or 450B, or their respective terminal blocks. In an example, an exposed conductor, such as an electrode 424 can be used to apply a voltage, or inject a current, such as into the region adjacent to the first or second seal plugs 440A or 440B. For example, such an applied voltage or injected current can couple between the electrode 424 and one or more of the first or second set screws 450A or 450B, or their respective terminal blocks, such as through an unwanted local conduction path near the header 400, thus failing an isolation test. In an example, the electrode 424 can be commonly shared with one or more other circuits, such as included in the IMD. In an example, the electrode 424 can be an indifferent electrode, such as used to monitor one or more of a thoracic or cardiac impedance, as discussed in the previously incorporated '728 impedance measurement application discussed in FIG. 2.

In an example, a lead can include multiple conductors (e.g., multiple concentric or adjacent flexible conductors insulated from each other within the lead). In an example of a multi-conductor lead, a first set screw 450A can be used such as to mechanically secure a distal tip electrode connection (e.g., as shown in FIG. 1). For example, a spring clip or other contact can be used in addition to or instead of a second set screw 450B, such as to contact a ring or coil electrode connection, such as provided by the multi-conductor lead. Since the first set screw 450A can be the primary mechanical anchor for the lead connection to the header block 400, the second set screw 450B can be unnecessary. Similarly, in an example, a set screw can be used to secure the ring or coil electrode connection, and a spring clip can be used to electrically contact the distal tip electrode connection.

FIG. 5 illustrates generally an example of a section view of a portion of an implantable medical device, such as including a header block 500, a first set screw 550A, a seal plug 540B, a second set screw 550B, and an electrode 524 (e.g., an isolation test electrode, such as used by the isolation test circuit of FIG. 2). In FIG. 5, the first seal plug 440A of FIG. 4 can be absent (or otherwise damaged as discussed below), thus allowing set screw 550A or a respective terminal block 560A to be at least partially exposed to conductive bodily fluid or tissue. In an example, one or more of the circuits or techniques discussed in FIG. 1, 2, 3A-B, 4, or 6 can be used, such as to detect the missing seal plug, or one or more other defects, such as providing an unwanted conductive path, such as through body tissue or fluid, such as between set screws 550A or 550B, or their respective terminal blocks. For example, instead of being absent, one or more seal plugs, such as the seal plug 540B can be electrically or mechanically compromised or physically damaged. The damage can include the seal plug 540B being gouged, crimped, deformed, torn or otherwise breached, such as during manufacturing or due to manipulation before or during implant, such as by mishandling of a torque wrench used for tightening the set screw 550B through a slit in the seal plug 540B, or by use of an incorrect torque wrench or other inappropriate tool.

In an example, a lead can include multiple conductors (e.g., multiple concentric or adjacent flexible conductors insulated from each other within the lead). In an example of a multi-conductor lead, a first set screw 550A can be used such as to mechanically secure a distal tip electrode connection (e.g., as shown in FIG. 1). For example, a spring clip or other contact can be used in addition to or instead of a second set screw 550B, such as to contact a ring or coil electrode connection, such as provided by the multi-conductor lead. Since the first set screw 550A can be the primary mechanical anchor for the lead connection to the header block 500, the second set screw 550B can be unnecessary. Similarly, in an example, a set screw can be used to secure the ring or coil electrode connection, and a spring clip can be used to electrically contact the distal tip electrode connection.

In an example, a second electrode, such as a second isolation test electrode can be located near or within a cavity in the header block 500, such as below a seal plug (e.g., between the seal plug and set screw). In another example, two seal plugs can be inserted into the cavity, and the second electrode can be between two seal plugs. For example, the second electrode can be used to independently verify the isolation between the interior of the cavity and the set screw (e.g., to verify the integrity of the lower seal plug), or between the interior of the cavity and the exterior of the header block (e.g., to verify the integrity of the upper seal plug). In an example, an isolation test stimulus signal can be applied, such as between the electrode 524, and the second electrode between the two seal plugs located in a single cavity. In another example, instead of two seal plugs in a single cavity, a single seal plug can be vertically elongated, such as including one or more lateral apertures, such as opening into an otherwise sealed interior portion of the seal plug. The one or more lateral apertures can be located near the second electrode, such as when the electrode is located within or near a side wall of the cavity, such as to allow an isolation test of the interior portion of the elongated seal plug.

Figure 6:
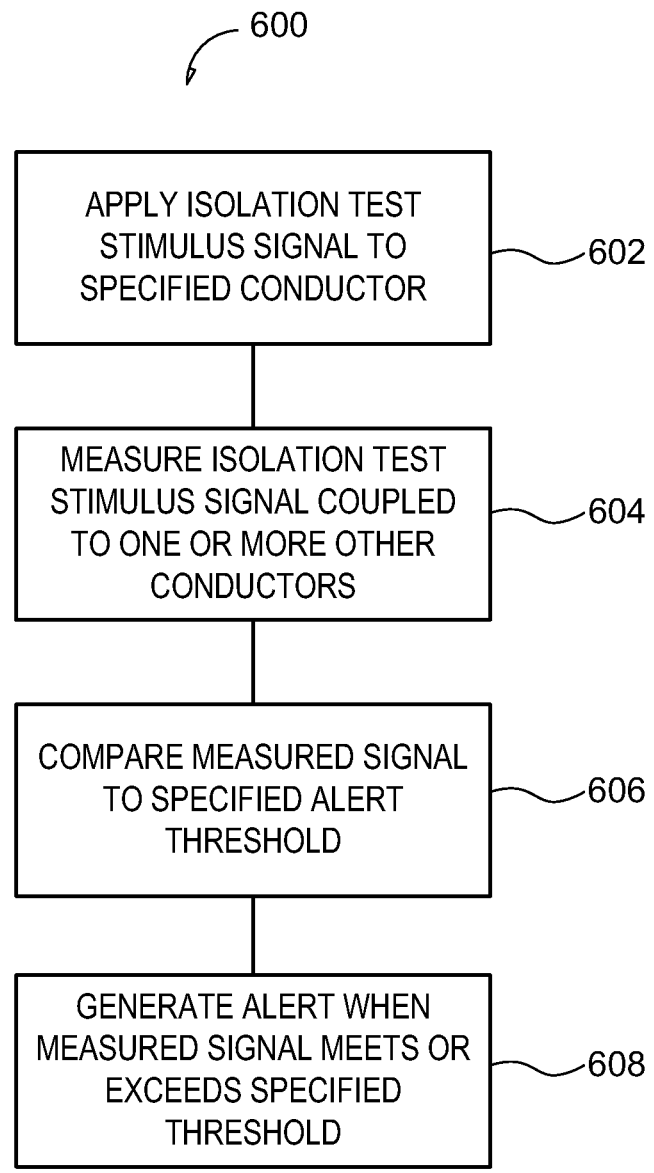
FIG. 6 illustrates generally an example of applying an isolation test stimulus signal to a specified electrode, and measuring an amount of the isolation test stimulus signal coupled to one or more other electrodes.

FIG. 6 illustrates generally an example 600 of testing isolation between one or more conductors. For example, at 602, a test stimulus signal can be applied to specified conductor, such as using one or more of the circuits or techniques of FIGS. 1-5, such as the isolation test circuit of FIG. 2. At 604, if the isolation test signal (e.g., an applied voltage or injected current) is coupled to a nearby conductor (e.g., between a stimulus electrode on or near an implantable medical device header block and one or more other exposed conductors nearby), a coupled voltage or current can be measured. In an example, at 606, the measured signal can be compared to a specified threshold, such as a specified alert threshold. At 608, an alert can be generated, such as if the coupled signal (e.g., the measured voltage or current) meets or exceeds the specified alert threshold, such as discussed in FIGS. 1-2.

Figure 7:
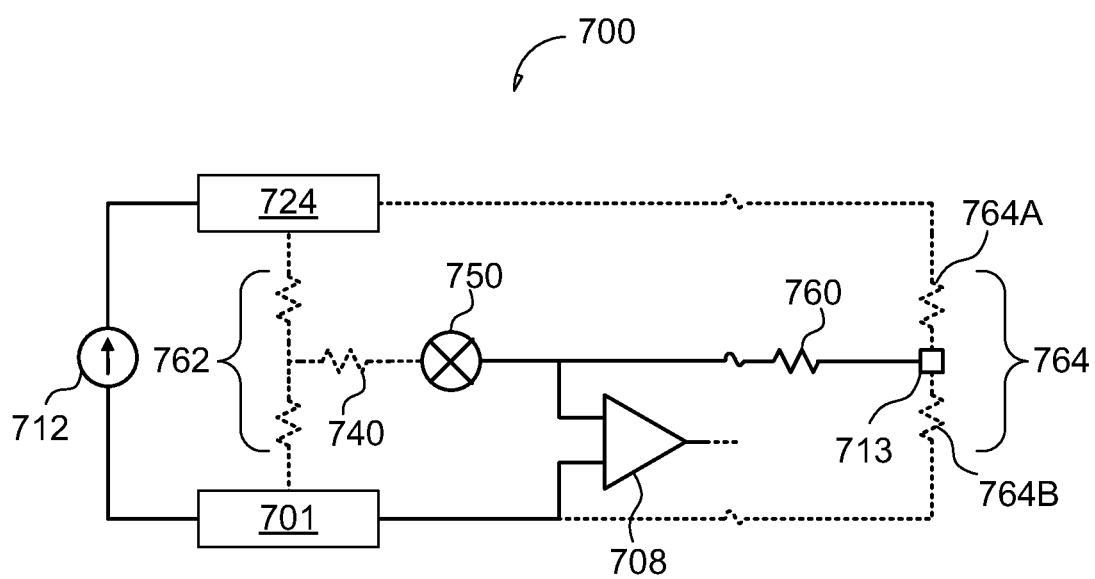
FIG. 7 illustrates generally an illustrative example including various resistances that can be measured.

FIG. 7 illustrates generally an illustrative example of an apparatus 700 that can be used to measure various resistances. Such resistances can be measured such as by using the isolation test circuit discussed in the examples of FIGS. 1-6. In the illustrative example of FIG. 7, the apparatus 700 can include portions of an isolation test circuit, such as discussed in FIGS. 1-6. The isolation test circuit can include a current source 712 (e.g., a stimulus generator circuit), such as configured to provide a pulsed or AC current stimulus. Such stimulus can be provided (e.g., injected) between a housing conductor 701 (e.g., a titanium portion of an IMD or other ambulatory medical device housing) and a common electrode 724, such as located in or near a header of the IMD.

In an example, a measurement circuit 708, such as including one or more amplifiers or digital-to-analog-converters can sample or otherwise measure a voltage, such as developed across a set-screw 750 (or other interconnection) and the housing conductor 701. In an example, the measurement circuit 708 can be commonly-shared with or otherwise similarly configured to a sense amplifier configured to measure cardiac electrical activity, or as generally used for measuring a voltage developed during a lead impedance measurement. In the illustrative example of FIG. 7, the housing conductor 701 can be commonly-shared as both a current injection electrode, and as an electrode for measurement of an induced voltage in response to the current injection. Such a configuration can provide better sensitivity than using a bipolar voltage measurement at two electrodes both located distally from the housing 701 and common electrode 724. Thus, in an example, one or more of the following electrode configurations can be tested, such as measuring the voltage developed between each electrode's corresponding set-screw 750 and the housing 701: right atrial tip (RAT) to housing 701; right ventricular tip (RVT) to housing 701; right atrial ring (RAR) to housing 701; right ventricular ring (RVR) to housing 701; left ventricular distal (LVD) to housing 701; left ventricular proximal (LVP) to can; or one or more other electrode configurations. In an example, an impedance measurement can be made to determine if a lead assembly or other electrodes are connected to the set-screw 750, and in response, isolation testing can be performed for leads or electrodes identified as present using information provided by the impedance measurement.

For example, in FIG. 7, a first resistive contribution 762 can be provided by the leakage path between common electrode 724 and the housing 701. In an example where the set-screw 750 is well-insulated from the housing 701 or common electrode 724 (e.g., a non-fault condition), the developed voltage at the measurement circuit 708 can be relatively small. A leakage resistance 740 to the set-screw 750 can be high (e.g., hundreds of kiloOhms or megaOhms).

In the example of FIG. 7, a second resistive contribution 764 can provide another path for current to induce a detectable voltage between the set-screw 750 and the conductive housing 701, such as due to a "far-field" potential (e.g., between a tip electrode 713 and housing 701) induced from the current injected by the current source 712. Generally, the first resistive contribution 762 can be a lower resistance (e.g., locally between the common electrode 724 and the housing 701), than the second resistive contribution 764 that includes more resistance from body tissue between the tip electrode 713 and the housing 701 or common electrode 724.

However, the divider formed by a combination of the second resistive contribution 764 and an implantable lead resistance 760 can "short out" the higher resistance of the path including the first resistance contribution 762 and the leakage resistance 740, because the leakage resistance 740 is much higher than the lead resistance 760 in a non-fault condition. In contrast, during a fault condition, the developed voltage induced between the set-screw 750 and the housing 701 can be greater when a "near-field" shunt path is provided by a low leakage resistance 740.

In an illustrative example, a ratio of the two resistances included in the second resistive contribution 764, respectively 764A and 764B, can be inversely related to a ratio or relative area of the tip common electrode 724 as compared to the housing 701 area. Because the housing 701 area is relatively large and the common electrode 724 area is comparatively small, the resistance between the tip electrode 713 and the housing 701 can be much smaller than the resistance between the tip electrode 713 and the common electrode 724. Thus, in the absence of any low resistance path between the set screw 750 and the common electrode 724, or the housing 701, the voltage across the measurement circuit 708 can be very small.

In contrast, such as during a fault, the leakage resistance 740 can be very small, and the voltage at the set screw 750 can thus be dominated by the potential gradient provided between the common electrode 724 and the housing 701, during testing.

For example, even if the two resistances comprising the first resistance 762 are about equal, half of a stimulus voltage applied between the common electrode 724 and the housing 701 would be applied to leakage resistance 740. The resulting leakage current through leakage resistance 740 would be dropped across the resistance 760, elevating the voltage into the measurement circuit 708, and if the leakage level is sufficient, providing a detectably larger voltage than the comparatively small voltage due to the far-field effect of the tip electrode 713 and second resistance contribution 764. Thus, using the housing electrode 701 can provide a relatively sensitive measurement configuration because both the housing 701 and common electrode 724 can be located near the site of a likely fault, but such a configuration will be relatively insensitive to the far-field voltage developed at the tip electrode 713 in a non-fault condition.

In an example, such as in response to impedance, voltage, or current information indicative of an isolation failure (e.g., a failing or leaky seal plug, etc.), one or more other parameters can be stored in addition to the impedance, voltage, or current information, such as information about a posture or a physical activity level (e.g., as measured by one or more of an accelerometer or a respiration sensor, for example). Such other parameters can be measured or stored at or near the time of the detected failure, such as for later presentation or analysis, such as to help in debugging or otherwise identifying ambulatory failures (e.g., an intermittent failure occurring only under certain ambulatory conditions). In an example, one or more of a therapy delivery or physiologic monitoring configuration can be adjusted, such as in response to information provided by the isolation test circuit. For example, if a particular electrode combination is implicated in an isolation test failure, a different electrode configuration can be automatically selected for further therapy delivery or monitoring, such as to avoid using one or more electrodes indicated as failing the isolation test. Such isolation testing can include using one or more examples (e.g., apparatus or techniques) such as discussed above in relation to FIGS. 1-7.

Various Notes and Examples

In Example 1, an implantable medical device can include a hermetically-sealed implantable housing, an exposed first conductor located on or near the housing, at least one insulated second conductor located near the exposed first conductor, and an isolation test circuit configured to provide a test stimulus to the exposed first conductor and configured to measure a portion of the test stimulus coupled to the second conductor. In this example, the isolation test circuit can include a comparator configured to compare the portion of the test stimulus coupled to the second conductor to a specified threshold value, and a controller circuit configured to trigger an alert to a user in response to the comparison when the portion of the stimulus coupled to the second conductor exceeds the specified threshold value.

In Example 2, the isolation test circuit of the subject matter of Example 1 can optionally include a test stimulus generator comprising a current source, and the test stimulus signal includes at least one current pulse generated by the current source, the current source configured to selectively inject the current at least between the first and second conductors.

In Example 3, the isolation test circuit of the subject matter of any one or more of Examples 1-2 can optionally include a measurement circuit configured to measure a voltage developed between the first and second conductors.

In Example 4, the controller circuit of the subject matter of any one or more of Examples 1-3 can be optionally configured to determine an impedance between the first and second conductors using information about the injected current and the measured voltage.

In Example 5, the controller circuit of the subject matter of any one or more of Examples 1-4 can be optionally configured to determine a baseline impedance between the first and second conductors using at least two impedance determinations, and can be configured to determine a relative indication of impedance information using a present impedance determination and one or more previous impedance determinations, or the baseline.

In Example 6, the controller circuit of the subject matter of any one or more of Examples 1-5 can be optionally configured to trigger the alert to the user when the relative indication of impedance information is outside a relative indication range; and wherein the relative indication range is selected from a list including a standard deviation range, a ratio range, a percentage range, or a variance range.

In Example 7, the subject matter of any one or more of Examples 1-6 optionally includes an isolation test circuit including a magnetic detector. In this example, the controller circuit can be coupled to the magnetic detector and configured to automatically trigger an isolation test between the first and second conductors, such as in response to a signal from the magnetic detector when the magnetic detector is or has been exposed to a magnetic field having an intensity above a specified threshold.

In Example 8, the subject matter of any one or more of Examples 1-7 optionally includes a header block configured to receive one or more implantable lead assemblies; and wherein the header block includes the insulated second conductor, the insulation including a cavity for a seal plug.

In Example 9, the isolation test circuit of the subject matter of any one or more of Examples 1-8 can be optionally configured to detect at least one of a missing seal plug or an insulation failure near the second conductor when the specified threshold is exceeded, using the coupled portion of the test stimulus signal as measured by the isolation test circuit, when the implantable medical device is implanted.

In Example 10, the isolation test circuit of the subject matter of any one or more of Examples 1-9 can be optionally configured to measure a baseline voltage developed across the first and second conductors using the measurement circuit without requiring use of the stimulus circuit, and the comparator can be configured to compare the baseline voltage with a specified baseline threshold voltage value. In this example, the controller circuit can be configured to trigger an alert to a user in response to the comparison when the baseline voltage exceeds the specified baseline threshold voltage value.

In Example 11, an implantable medical device can include a hermetically-sealed implantable housing, an exposed first conductor located on or near the housing, at least one insulated second conductor located near the exposed first conductor, an isolation test circuit configured to provide a test stimulus to the exposed first conductor and configured to measure a portion of the test stimulus coupled to the second conductor. In this example, the isolation test circuit can include a comparator configured to compare the portion of the test stimulus coupled to the second conductor to a specified threshold value, a controller circuit configured to trigger an alert to a user in response to the comparison when the portion of the stimulus coupled to the second conductor exceeds the specified threshold value, and a magnetic detector coupled to the controller circuit and wherein the controller circuit is configured to provide a trigger to the isolation test circuit, the trigger causing the isolation test circuit to measure the coupled portion between the first and second conductors when the magnetic detector is exposed to a magnetic field having an intensity above a specified threshold.

Example 12 can include, or can optionally be combined with the subject matter of one or any combination of Examples 1-11 to include, subject matter (such as a method, a means for performing acts, or a machine-readable medium including instructions that, when performed by the machine, cause the machine to perform acts) comprising providing an isolation test between a first conductor located on or near a hermetically-sealed implantable medical device housing and at least one insulated second conductor located near the exposed first conductor, the isolation test including providing a test stimulus to the exposed first conductor using an isolation test circuit included in the implantable medical device housing, measuring a portion of the test stimulus coupled to the insulated second conductor, comparing the measured portion of the test stimulus to a specified threshold value, and in response, triggering an alert to a user using a control circuit included within the implantable medical device housing when the comparing the measured portion indicates that the measured portion exceeds the specified threshold value.

In Example 13, the subject matter of Example 12 can optionally include providing at least one current pulse generated by a current source included in the isolation test circuit, the at least one current pulse injected at least between the first and second conductors.

In Example 14, the subject matter of any one or more Examples 12-13 can optionally include measuring a voltage developed between the first and second conductors in response to the at least one current pulse injected between the first and second conductors.

In Example 15, the subject matter of any one or more of Examples 12-14 can optionally include determining an impedance between first and second conductors using information about the injected current and the measured voltage.

In Example 16, the subject matter of any one or more of Examples 12-15 can optionally include determining a baseline impedance between the first and second conductors using at least two impedance determinations, and determining a relative indication of impedance information using a present impedance determination and one or more previous impedance determinations, or the baseline.

In Example 17, the subject matter of any one or more of Examples 12-16 can optionally include triggering an alert to the user when the relative indication of impedance information is outside a relative indication range, the relative indication range selected from a list including a standard deviation range, a ratio range, a percentage range, or a variance range.

In Example 18, the subject matter of any one or more of Examples 12-17 can optionally include detecting a magnetic field using a magnetic detector included in the implantable medical device housing, and triggering the isolation test between at least the first and second conductors using the controller circuit using information from the magnetic detector when the magnetic detector is or has been exposed to a magnetic field having an intensity above a specified threshold.

In Example 19, the subject matter of any one or more of Examples 12-18 can optionally include measuring the portion of the stimulus coupled to the second conductor when the second conductor is included as a portion of a header block attached to the housing of the implantable medical device, the header block configured to receive one or more implantable lead assemblies, and including a cavity for a seal plug.

In Example 20, the subject matter of any one or more of Examples 12-19 can optionally include detecting at least one of a missing seal plug or an insulation failure near the second conductor when the specified threshold value is exceeded as indicated by the comparing of the measured portion of the stimulus coupled to the second conductor. Example 20 can include storing information about one or more of a patient activity level, or a patient posture, corresponding to at least a portion of an interval of time where the isolation test stimulus is provided.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An implantable medical device, comprising:
a hermetically-sealed implantable housing;
an exposed first conductor located on or near the housing;
at least one insulated second conductor located near the exposed first conductor; and
an isolation test circuit configured to provide a test stimulus to the exposed first conductor and configured to measure a portion of the test stimulus coupled to the second conductor, the isolation test circuit including:
a comparator configured to compare the portion of the test stimulus coupled to the second conductor to a specified threshold value; and
a controller circuit configured to trigger an alert to a user in response to the comparison when the portion of the stimulus coupled to the second conductor exceeds the specified threshold value.

2. The implantable medical device of claim 1, wherein the isolation test circuit includes a test stimulus generator comprising a current source, and wherein the test stimulus signal includes at least one current pulse generated by the current source, the current source configured to selectively inject the current at least between the first and second conductors.

3. The implantable medical device of claim 2, wherein the isolation test circuit includes a measurement circuit configured to measure a voltage developed between the first and second conductors.

4. The implantable medical device of claim 3, wherein the controller circuit is configured to determine an impedance between the first and second conductors using information about the injected current and the measured voltage.

5. The implantable medical device of claim 4, wherein the controller circuit is configured to determine a baseline impedance between the first and second conductors using at least two impedance determinations; and wherein the controller circuit is configured to determine a relative indication of impedance information using a present impedance determination and one or more previous impedance determinations, or the baseline.

6. The implantable medical device of claim 5, wherein the controller circuit is configured to trigger the alert to the user when the relative indication of impedance information is outside a relative indication range; and wherein the relative indication range is selected from a list including a standard deviation range, a ratio range, a percentage range, or a variance range.

7. The implantable medical device of claim 1, wherein the isolation test circuit comprises a magnetic defector; and wherein the controller circuit is coupled to the magnetic detector and configured to automatically trigger an isolation test between the first and second conductors in response to a signal from the magnetic detector when the magnetic detector is or has been exposed to a magnetic field having an intensity above a specified threshold.

8. The implantable medical device of claim 1, comprising a header block configured to receive one or more implantable lead assemblies; and wherein the header block includes the insulated second conductor, the insulation including a cavity for a seal plug.

9. The implantable medical device of claim 8, wherein the isolation test circuit is configured to detect at least one of a missing seal plug or an insulation failure near the second conductor when the specified threshold is exceeded, using the coupled portion of the test stimulus signal as measured by the isolation test circuit, when the implantable medical device is implanted.

10. The implantable medical device of claim 8, wherein the isolation test circuit is configured to measure a baseline voltage developed across the first and second conductors using the measurement circuit without requiring use of the stimulus circuit;

wherein the comparator is configured to compare the baseline voltage with a specified baseline threshold voltage value; and wherein the controller circuit is configured to trigger an alert to a user in response to the comparison when the baseline voltage exceeds the specified baseline threshold voltage value.

11. An implantable medical device, comprising:
a hermetically-sealed implantable housing;
an exposed first conductor located on or near the housing;
at least one insulated second conductor located near the exposed first conductor; and
an isolation test circuit configured to provide a test stimulus to the exposed first conductor and configured to measure a portion of the test stimulus coupled to the second conductor, the isolation test circuit including:
a comparator configured to compare the portion of the test stimulus coupled to the second conductor to a specified threshold value;
a controller circuit configured to trigger an alert to a user in response to the comparison when the portion of the stimulus coupled to the second conductor exceeds the specified threshold value;
a magnetic detector coupled to the controller circuit and wherein the controller circuit is configured to provide a trigger to the isolation test circuit, the trigger causing the isolation test circuit to measure the coupled portion between the first and second conductors when the magnetic detector is exposed to a magnetic field having an intensity above a specified threshold.

12. A method, comprising:
providing an isolation test between a first conductor located on or near a hermetically-sealed implantable medical device housing and at least one insulated second conductor located near the exposed first conductor, the isolation test including:
providing a test stimulus to the exposed first conductor using an isolation test circuit included in the implantable medical device housing;
measuring a portion of the test stimulus coupled to the insulated second conductor; and
comparing the measured portion of the test stimulus to a specified threshold value; and
in response triggering an alert to a user using a control circuit included within the implantable medical device housing when the comparing the measured portion indicates that the measured portion exceeds the specified threshold value.

13. The method of claim 12, wherein the providing the test stimulus includes providing at least one current pulse generated by a current source included in the isolation test circuit, the at least one current pulse injected at least between the first and second conductors.

14. The method of claim 13, wherein the measuring a portion of the test stimulus includes measuring a voltage developed between the first and second conductors in response to the at least one current pulse injected between the first and second conductors.

15. The method of claim 14, comprising determining an impedance between first and second conductors using information about the injected current and the measured voltage.

16. The method of claim 15, comprising determining a baseline impedance between the first and second conductors using at least two impedance determinations; and determining a relative indication of impedance information using a present impedance determination and one or more previous impedance determinations, or the baseline.

17. The method of claim 16, wherein the triggering the alert using the controller circuit includes triggering an alert to the user when the relative indication of impedance information is outside a relative indication range, the relative indication range selected from a list including a standard deviation range, a ratio range, a percentage range, or a variance range.

18. The method of claim 12, comprising detecting a magnetic field using a magnetic detector included in the implantable medical device housing; and triggering the isolation test between at least the first and second conductors using the controller circuit using information from the magnetic detector when the magnetic detector is or has been exposed to a magnetic field having an intensity above a specified threshold.

19. The method of claim 12, wherein the measuring the portion of the stimulus coupled to the second conductor includes measuring the portion of the stimulus coupled to the second conductor when the second conductor is included as a portion of a header block attached to the housing of the implantable medical device, the header block configured to receive one or more implantable lead assemblies, and including a cavity for a seal plug.

20. The method of claim 19, wherein the providing the isolation test includes detecting at least one of a missing seal plug or an insulation failure near the second conductor when the specified threshold value is exceeded as indicated by the comparing of the measured portion of the stimulus coupled to the second conductor; and wherein the method comprises storing information about one or more of a patient activity level, or a patient posture, corresponding to at least a portion of an interval of time where the isolation test stimulus is provided.

* * * * *